(12) United States Patent
Mercier et al.

(10) Patent No.: US 7,319,117 B2
(45) Date of Patent: Jan. 15, 2008

(54) METHOD FOR PREPARING A WATER/OIL/WATER MULTIPLE EMULSION

(75) Inventors: Jean-Michel Mercier, Gouvieux (FR); Emmanuelle Vallier, Aubervilliers (FR)

(73) Assignee: Rhodia Chimie (FR)

( * ) Notice: Subject to any disclaimer, the term of this patent is extended or adjusted under 35 U.S.C. 154(b) by 793 days.

(21) Appl. No.: 10/498,211

(22) PCT Filed: Dec. 2, 2002

(86) PCT No.: PCT/FR02/04127

§ 371 (c)(1),
(2), (4) Date: Jun. 9, 2004

(87) PCT Pub. No.: WO03/049846

PCT Pub. Date: Jun. 19, 2003

(65) Prior Publication Data

US 2005/0019352 A1    Jan. 27, 2005

(30) Foreign Application Priority Data

Dec. 11, 2001    (FR) .................................. 01 15982

(51) Int. Cl.
*B01F 3/00*    (2006.01)
*B01F 3/08*    (2006.01)

(52) U.S. Cl. ........................................ 524/501; 524/56
(58) Field of Classification Search ................ 524/501, 524/56

See application file for complete search history.

(56) References Cited

U.S. PATENT DOCUMENTS

| | | | |
|---|---|---|---|
| 5,100,951 A | * | 3/1992 | Fillipo et al. ................ 524/501 |
| 7,101,931 B2 | * | 9/2006 | Lannibois-Drean et al. 524/801 |
| 7,214,717 B1 | * | 5/2007 | Jaques Bibette et al. ..... 516/54 |

* cited by examiner

*Primary Examiner*—Kelechi C. Egwim
(74) *Attorney, Agent, or Firm*—Hunton & Williams LLP

(57) ABSTRACT

The invention concerns a method for preparing a multiple emulsion comprising an invert emulsion consisting of an internal aqueous phase dispersed in an internal organic phase, dispersed in an external aqueous phase: the internal aqueous phase comprising optionally at least a hydrophilic active substance; the internal organic phase comprising optionally at least a hydrophobic active substance; the invert emulsion comprising at least an internal surfactant and/or at least an internal amphiphilic polymer; the external aqueous phase comprising optionally at least a hydrophilic active substance and at least an external surfactant and/or an external amphiphilic polymer.

20 Claims, No Drawings

METHOD FOR PREPARING A WATER/OIL/WATER MULTIPLE EMULSION

This application is an application under 35 U.S.C. Section 371 of International Application Number PCT/FR02/04127 filed on Dec. 02, 2002.

The present invention relates to a process for preparing a water/oil/water multiple emulsion, in which, advantageously, only one reactor is used.

Standard processes for preparing water/oil/water multiple emulsions consist first in preparing the water-in-oil inverse emulsion in a first reactor. Next, an outer aqueous phase is prepared in a second reactor. The inverse emulsion previously obtained is then added to the outer aqueous phase. This type of process poses no major problems, especially when the inverse emulsion is relatively nonviscous, which is reflected by the fact that the oil constituting the organic phase of the inverse emulsion is fluid, or alternatively when the concentration of aqueous phase dispersed in the organic phase of the multiple emulsion remains relatively low (less than 50% by weight of the combination), or even a combination of both. However, it has a drawback due to the fact that two reactors are necessary to perform this operation, one of which will require the installation of specific means to ensure that it is correctly cleaned between two production runs.

However, when the difference between the viscosity of the inverse emulsion and that of the outer aqueous phase to which it is added is large, the process described above becomes more complex to perform and gives a less satisfactory result.

Firstly, one of the problems lies in the difficult manipulability of inverse emulsions of high viscosity.

Moreover, stirring difficulties are encountered. Specifically, under the conditions in which the difference in viscosity between the aqueous and organic phases is large, a reduction in the efficacy of stirring is observed: in other words, the shear produced by stirring, which is transmitted via the continuous phase of the emulsion, is much less efficient. Consequently, in order to obtain a satisfactory droplet size, it is necessary to use stirring means that develop considerably more energy than the standard means. However, the use of stirring of this type is not without consequence on the inverse emulsion, since, under such stirring conditions, the droplets of the inverse emulsion may themselves be sheared, entailing an appreciable risk of release of the active material encapsulated in the inner aqueous phase of the multiple emulsion.

A solution to this implementation problem consists in using heat-thickening polymers. These polymers, when introduced into the outer aqueous phase, develop a high viscosity when the temperature of the aqueous medium in which they are present is higher than their threshold temperature. More particularly, these polymers are soluble in water at room temperature and, beyond the threshold temperature, a portion of the polymer becomes hydrophobic (heat-sensitive portion): the polymer thus forms a physical network at the microscopic scale, which is reflected at the macroscopic scale by an increase in viscosity. Consequently, the difference in viscosity between the outer aqueous phase and the inverse emulsion is limited, and an increase in the efficacy of the shear is observed, via better transfer from the continuous phase of the emulsion to the discontinuous phase. Consequently, the stirring means that may be used may be less powerful and the problem of release of the active material enclosed in the inner aqueous phase is also limited.

A first subject of the present invention consists in providing an alternative to the use of heat-thickening polymers.

Moreover, another object of the present invention is to propose a process for preparing water/oil/water multiple emulsions that can be performed with multiple emulsions having broad viscosity ranges.

Another object of the invention is to have available a process that effectively avoids any release of the active material encapsulated in the inner aqueous phase, during the preparation of the emulsion.

These aims and others are achieved by the present invention, one subject of which is thus a process for preparing a multiple emulsion comprising an inverse emulsion consisting of an inner aqueous phase dispersed in an inner organic phase; the inverse emulsion being dispersed in an outer aqueous phase;

the inner aqueous phase optionally comprising at least one hydrophilic active material; the inner organic phase optionally comprising at least one hydrophobic active material;

the inverse emulsion comprising at least one inner surfactant and/or at least one inner amphiphilic polymer;

the outer aqueous phase comprising at least one outer surfactant and/or at least one outer amphiphilic polymer and optionally at least one hydrophilic active material;

the process according to the invention consisting in performing the following steps:

a) the inverse emulsion is prepared;
b) the outer aqueous phase is prepared;
c) the outer aqueous phase is introduced into the inverse emulsion, without stirring;
d) the mixture is stirred;
e) the concentrated multiple emulsion thus obtained is optionally diluted, by adding, with stirring, an aqueous dilution phase comprising at least one outer surfactant and/or at least one outer amphiphilic polymer, in order to obtain a dilute multiple emulsion.

The process according to the invention has the advantage of allowing access to multiple emulsions whose mean droplet size may be small although the operating conditions are in principle unfavorable, for instance the use of a concentrated inverse emulsion and/or an inverse emulsion whose organic phase is viscous.

Moreover, the process according to the invention no longer requires the use of two cascade reactors, as is the case for the standard processes. Consequently, the process according to the invention overcomes the problems associated with the manipulation (transfer) of the inverse emulsion into another reactor. Furthermore, the problems of cleaning the reactor used for the preparation of the inverse emulsion are solved in the case of the present invention, since the final multiple emulsion obtained is an emulsion whose outer phase is aqueous.

In addition, the process according to the invention can produce multiple emulsions of various concentrations. Specifically, not only is the multiple emulsion obtained after the process according to the invention in a concentrated form, but it may also undergo a subsequent dilution, without any difficulty or loss of size characteristics of the droplets of the multiple emulsion before dilution.

However, other advantages of the present invention will emerge more clearly on reading the description and examples that follow.

It is pointed out in the text hereinbelow that the term "polymers" is used to denote both homopolymers and copolymers.

Furthermore, to differentiate between the phases of the multiple emulsion and the various constituents thereof, the phases, surfactants and polymers present in the inverse emulsion will first be referred to as inner aqueous phase, inner organic phase and inner surfactant and/or inner amphiphilic polymer. Moreover, the phases, surfactants and polymers present in the outer aqueous phase of the multiple emulsion will be referred to as outer aqueous phase and outer surfactant and/or outer amphiphilic polymer. It is pointed out that if the outer aqueous phase of the multiple emulsion comprises a dispersed organic phase other than an inverse emulsion, this phase will be termed an outer organic phase.

For reasons of clarity of the description, the constituent components of the multiple emulsion will be detailed, and first the constituent components of the inverse emulsion.

Thus, as has been mentioned previously, the inner aqueous phase optionally comprises at least one hydrophilic active material.

This hydrophilic active material may be in a liquid form; in a form dissolved in a water-miscible solvent, for instance ethanol, propylene glycol or glycerol; or in a solid form.

The content of hydrophilic active material is more particularly between 0.1% and 50% by weight of the inner aqueous phase and preferably between 0.1% and 20% by weight of the inner aqueous phase.

Given the large number of fields in which the multiple emulsions according to the invention may be used, numerous active materials may be suitable for use in the invention.

As examples of active materials that may be used in cosmetics, mention may be made of substances that have a cosmetic effect, a therapeutic effect or any other substance that may be used for treating the skin and/or the hair.

Thus, active materials that may be used include skin and/or hair conditioners, especially such as polymers comprising quaternary ammoniums which may optionally be engaged in heterocycles (compounds of the quaternium or polyquaternium type, etc.); humectants; fixing (styling) agents more particularly chosen from polymers (homopolymers, copolymers or terpolymers, for instance acrylamide, acrylamide/sodium acrylate, polystyrene sulfonate, etc.), cationic polymers, polyvinylpyrrolidone, polyvinyl acetate, etc.

It is similarly possible to use dyes; astringents, which may be used in deodorants and which are more particularly aluminum or zirconium salts; antibacterial agents; antiinflammatory agents, anesthetics, sunscreens, etc.

Mention may also be made of α- and β-hydroxy acids, for instance citric acid, lactic acid, glycolic acid and salicylic acid; dicarboxylic acids, which are preferably unsaturated and containing 9 to 16 carbon atoms, for instance azelaic acid; vitamin C and its derivatives, especially-glycosyl and phosphate derivatives; biocides, especially cationic biocides (Glokill PQ and Rhodoquat RP50, sold by Rhodia Chimie), as active materials that are suitable in cosmetic formulations.

In the food sector, examples that may be mentioned include divalent calcium salts (phosphates, chlorides, etc.) used as crosslinking agent for texturing polymers, for instance alginates and carrageenans; sodium bicarbonate, inter alia.

In the field of plant-protection active materials, hydrophilic pesticides or hydrophilic nutrients that promote the growth and development of plants may be used.

Among the active materials that are suitable, mention may be made especially of the following herbicidal active materials, which may or may not be in the form of organic or mineral salts: aminophosphate or aminophosphonate derivatives, acifluorfen, asulam, benazolin, bentazon, bialaphos, bispyribac, bromacil, bromoxynil, chloramben, clopyralid, 2,4-D, 2,4-Db, dalapon, dicamba, dichlorprop, diclofop, difenzoquat, diquat, endothall, fenac, fenoxaprop, flamprop, fluazifop, fluoroglycofen, fluroxypyr, fomesafen, fosamine, haloxyfop, ioxynil, mcpa, mcpb, mecoprop, methylarsonic acid, naptalam, nonanoic acid, paraquat, picloram, sulfamic acid or mixtures thereof.

Preferably, the active material is chosen from aminophosphate and aminophosphonate derivatives, in the form of organic or mineral salts, for instance glyphosate, sulfosate or glufosinate.

As regards the field of exploitation or construction of petroleum or gas drilling wells, the present invention may be performed for hydrophilic active materials that may be used especially during cementation, completion, drilling and stimulation of wells (for example fracturing). As examples of active materials that may be used in this field, mention may be made of crosslinking catalysts for cement compositions, for instance lithium salts, such as the chloride or acetate. Mention may similarly be made of compounds that are capable, inter alia, of degrading polysaccharides, for instance carboxylic acids (especially citric acid), enzymes (especially cellulases) and oxidizing agents.

In the field of silicones, examples that may be mentioned include the calcium salts and the potassium salts, which are usually used as crosslinking agents.

As active materials that are suitable in the papermaking sector, mention may be made especially of calcium chloride and hydrochloric acid.

In accordance with one particularly advantageous embodiment, the inner aqueous phase may comprise at least one additive chosen from salts such as alkali metal or alkaline-earth metal halides (for instance sodium chloride or calcium chloride), or alkali metal or alkaline-earth metal sulfates (for instance sodium sulfate), or mixtures thereof. As possible additives of the inner aqueous phase, mention may also be made of sugars, for instance glucose, or polysaccharides, especially such as dextran, or mixtures thereof.

The concentration of additive of the salt type, when this additive is present, is more particularly between 0.05 and 1 mol/l and preferably 0.1 to 0.4 mol/l.

The concentration of additive of the sugar and/or polysaccharide type is such that the osmotic pressure of the inner aqueous phase comprising the sugar and/or polysaccharide corresponds to the osmotic pressure of an inner aqueous phase comprising 0.05 to 1 mol/l of salt.

The inner organic phase of the emulsion is chosen from compounds that are immiscible in an aqueous phase. The term "immiscible" means compounds whose solubility in an aqueous phase does not exceed 10% by weight, over a temperature range of between 20° C. and the temperature of preparation of the inverse emulsion and of the multiple emulsion.

Moreover, the compounds used as inner organic phase are advantageously chosen from those that are in a liquid form at the temperature of preparation of the inverse emulsion and of the multiple emulsion.

According to a first possibility, the inner organic phase comprises at least one organic oil, of animal, plant or mineral origin, and also waxes obtained from the same sources, or mixtures thereof.

As organic oils of animal origin, mention may be made, inter alia, of sperm whale oil, whale oil, sardine oil, herring oil, shark oil and cod liver oil; pig or sheep fat (tallow).

As waxes of animal origin, mention may be made of beeswax.

As examples of organic oils of plant origin, mention may be made, inter alia, of rapeseed oil, sunflower oil, groundnut oil, olive oil, walnut oil, maize oil, soybean oil, linseed oil, hemp oil, grapeseed oil, coconut oil, palm oil, cottonseed oil, babassu oil, jojoba oil, sesame seed oil, castor oil, cocoa butter and shea butter.

As waxes of plant origin, mention may be made of carnauba wax.

As regards the mineral oils, mention may be made, inter alia, of naphthenic oils, paraffinic oils (petroleum jelly) and polybutenes (for example, obtained via polymerization of the C fraction, the isobutene proportion of which is high: Napvis or Hyvis ranges from BP).

The paraffin waxes may similarly be suitable for preparing the emulsion.

The products derived from the alcoholysis of the above-mentioned oils or waxes may also be used.

It would not constitute a departure from the context of the present invention to use, as inner organic phase, at least one saturated or unsaturated fatty acid, at least one saturated or unsaturated fatty acid ester, at least one saturated or unsaturated fatty alcohol, or mixtures thereof.

More particularly, said acids, esters or alcohols contain 8 to 40 carbon atoms in the longest carbon-based chain, more particularly at least 10 carbon atoms and preferably at least 18 carbon atoms, and may comprise one or more conjugated or nonconjugated ethylenic unsaturations. Moreover, the acids esters or alcohols may comprise one or more hydroxyl groups.

Examples of saturated fatty acids that may be mentioned include palmitic acid, stearic acid and behenic acid.

Examples of unsaturated fatty acids that may be mentioned include myristoleic acid, palmitoleic acid, oleic acid, erucic acid, linoleic acid, linolenic acid, arachidonic acid and ricinoleic acid, and also mixtures thereof.

Fatty acid esters that may be mentioned include esters of the acids listed above, for which the portion derived from the alcohol contains 1 to 6 carbon atoms, for instance the methyl, ethyl, propyl, isopropyl, etc. esters.

Examples of alcohols that may be mentioned include those corresponding to the abovementioned acids.

The inner organic phase may similarly be chosen from monoglycerides, diglycerides and triglycerides.

The essential oils may also be used as inner organic phase. Among the compounds of this type that may be mentioned, without wishing to be limited thereto, are oils and/or essences of mint, of green mint, of peppermint, of menthol, of vanilla, of cinnamon, of laurel, of aniseed, of eucalyptus, of thyme, of sage, of cedar leaf, of nutmeg, of citrus (lemon, lime, grapefruit or orange) or of fruit (apple, pear, peach, cherry, plum, strawberry, raspberry, apricot, pineapple, grape, etc.), alone or as mixtures.

The inner organic phase may also be chosen from silicone oils.

According to one particular embodiment of the invention, the inner organic phase comprises at least one hydrophobic active material. Preferably, said hydrophobic active material is chosen from species that are compatible with the hydrophilic active material present in the inner aqueous phase and, if it is present, in the outer aqueous phase.

It should be noted that the organic phase itself may constitute the hydrophobic active material.

Said hydrophobic active materials are in liquid form, dissolved in an organic solvent that is miscible with the inner organic phase, or alternatively in the form of a solid dispersed in said phase.

More particularly, the active materials are such that their solubility in water does not exceed 10% by weight, in a temperature range of between 20° C. and the temperature of preparation of the inverse emulsion and of the multiple emulsion.

Moreover, active materials with a melting point of less than or equal to 100° C. and more particularly less than or equal to 80° C. may be used.

As examples of active materials that may be used in cosmetics, mention may be made of silicone oils belonging, for example, to the dimethicone family; lipophilic vitamins, for instance vitamin A and its derivatives, especially its esters, for instance the acetate, palmitate or propionate, vitamin B2, pantothenic acid, vitamin D and vitamin E; monoglycerides, diglycerides and triglycerides; bactericides; UV absorbers, for instance aminobenzoate derivatives of PABA and PARA type, salicylates, cinnamates, anthranilates, dibenzoylmethanes and camphor derivatives, and mixtures thereof.

Anti-aging agents may similarly be used. Examples of such agents that may especially be mentioned include retinoids, liposoluble vitamins, vitamin C derivatives, for instance the acetate, propionate and palmitate esters especially; ceramides, pseudoceramides, phospholipids, fatty acids, fatty alcohols, cholesterol and sterols, and mixtures thereof. As preferred fatty acids and fatty alcohols, mention may be made more particularly of those with linear or branched alkyl chains containing from 12 to 20 carbon atoms. This may especially be linoleic acid.

It is similarly possible to use anticellulite agents, especially such as isobutylmethylxanthine and theophylline; and also antiacne agents, for instance resorcinol, resorcinyl acetate, benzoyl peroxide and numerous natural compounds.

Flavorings, essential oils and fragrances may also be used as hydrophobic active material. Reference may be made to the lists of compounds given previously.

The antimicrobial agents may be chosen from thymol, menthol, triclosan, 4-hexylresorcinol, phenol, eucalyptol, benzoic acid, benzoyl peroxide and butyl paraben, and mixtures thereof.

As examples of active materials that are suitable for performing the invention, in the field of paints, mention may be made of alkyd resins, epoxy resins and masked or unmasked (poly)isocyanates.

In the paper sector, examples that may be mentioned include size resins and water-repellent resins, such as alkylketene dimer (AKD) or alkenyl-succinic anhydride (ASA).

In agrochemistry, the plant-protection active materials may be chosen from the family of α-cyano-phenoxybenzyl carboxylates or α-cyanohalophenoxy-carboxylates, the family of N-methylcarbonates comprising aromatic substituents, and active materials such as aldrin, azinphos-methyl, benfluralin, bifenthrin, chlorphoxim, chlorpyrifos, fluchloralin, fluroxypyr, dichlorvos, malathion, molinate, parathion, permethrin, profenofos, propiconazole, prothiofos, pyrifenox, butachlor, metolachlor, chlorimephos, diazinon, fluazifop-P-butyl, heptopargil, mecarbam, propargite, prosulfocarb, bromophos-ethyl, carbophenothion or cyhalothrin.

In the detergency sector, possible active materials that may be mentioned include silicone antifoams.

It is similarly possible to use active materials such as those included in the composition of material-working or material-bending lubricants. The active material is usually an oil, an oil derivative or a fatty acid ester.

The active material may also be chosen from organic solvents or mixtures of such solvents that are immiscible in water (solubility in water not exceeding 10% by weight, within a temperature range of between 20° C. and the temperature of preparation of the inverse emulsion and of the multiple emulsion), especially such as those used for cleaning or stripping, such as aromatic petroleum fractions, terpene compounds, for instance D- or L-limonenes, and also solvents such as Solvesso®. Aliphatic esters, for instance the methyl esters of a mixture of acetic acid, succinic acid and glutaric acid (mixture of acids obtained as byproducts of Nylon synthesis), are also suitable as solvents; hydrocarbon-based oils, such as liquid petroleum jelly, and chlorinated solvents are also suitable.

In the case where the inner organic phase comprises one or more hydrophobic active materials, which are different than the organic phase, their total content more particularly represents 10% to 50% by weight of said inner organic phase.

The inverse emulsion also comprises at least one inner surfactant and/or at least one inner amphiphilic polymer.

According to a first variant, the surfactant and/or the amphiphilic polymer satisfy Bancroft's rule. In other words, the fraction of the surfactant or polymer that is soluble in the inner organic phase (continuous phase of the inverse emulsion) is greater than the fraction of the surfactant or polymer that is soluble in the inner aqueous phase (dispersed phase of the inverse emulsion). In this case, it will be said that the surfactant and/or the polymer is (are) rather located in the inner organic phase.

More particularly, these surfactants and polymers that satisfy Bancroft's rule are chosen from compounds of this type that satisfy both of the following conditions:
  when they are mixed with the inner organic phase (i.e. the continuous phase of the inverse emulsion) at a concentration of between 0.1% and 10% by weight of said phase and between 20 and 30° C., they are in the form of a solution in all or part of the indicated concentration range;
  when they are mixed with the inner aqueous phase (i.e. the dispersed phase of the inverse emulsion) at a concentration of between 0.1% and 10% by weight of said phase and between 20 and 30° C., they are in the form of a dispersion in all or part of the indicated concentration range.

More particularly, the surfactant and/or amphiphilic polymer are chosen from nonionic surfactants and/or amphiphilic block polymers.

As examples of nonionic surfactants that may be included in the composition of the inverse emulsion, mention may be made, alone or as a mixture, of surfactants chosen from:
  alkoxylated fatty alcohols
  alkoxylated mono-, di- and triglycerides
  alkoxylated fatty acids
  optionally alkoxylated sorbitan esters
  alkoxylated fatty amines
  alkoxylated bis(1-phenylethyl)phenols
  alkoxylated tris(1-phenylethyl)phenols
  alkoxylated alkylphenols the number of alkoxylated units (ethoxylated, propoxylated or butoxylated units or mixtures thereof) is such that the HLB value is less than or equal to 8.

The alkoxylated fatty alcohols generally contain from 6 to 22 carbon atoms, the alkoxylated units being excluded from these numbers.

The alkoxylated mono-, di- and triglycerides may be mono-, di- and triglycerides of plant or animal origin.

The optionally alkoxylated sorbitan esters are cyclized sorbitol esters of a fatty acid containing from 10 to 20 carbon atoms, for instance lauric acid, stearic acid or oleic acid.

The alkoxylated fatty amines generally contain from 10 to 22 carbon atoms, the alkoxylated units being excluded from these numbers.

The alkoxylated alkylphenols generally contain one or two linear or branched alkyl groups containing 4 to 12 carbon atoms. Examples that may especially be mentioned include octyl, nonyl and dodecyl groups.

As regards the amphiphilic block polymer, it comprises at least two blocks and more particularly at least one hydrophobic block and at least one neutral, anionic or cationic hydrophilic block.

In the case where the amphiphilic polymer comprises at least three blocks, and more particularly three blocks, the polymer is preferably linear. In addition, the hydrophobic blocks are advantageously located at the ends.

In the case where the polymers comprise more than three blocks, these blocks are preferably in the form of grafted polymers or comb polymers.

In the text hereinbelow, although this constitutes a misuse of language, the term "amphiphilic block polymer" will be used without preference for linear block polymers and grafted or comb polymers.

Said amphiphilic polymers may advantageously be obtained by living or controlled free-radical polymerization. As nonlimiting examples of living or controlled polymerization processes, reference may be made especially to patent applications WO 98/58974 (xanthate), WO 97/01478 (dithioesters), WO 99/03894 (nitroxides) and WO 99/31144 (dithiocarbamates).

The amphiphilic polymers may also be obtained via cationic or anionic polymerization.

They may similarly be prepared using ring-opening polymerizations (especially anionic or cationic polymerizations) or via chemical modification of the polymer.

The grafted or comb polymers may also be obtained via direct grafting methods and copolymerization.

Direct grafting consists in polymerizing the selected monomer(s) via a free-radical route, in the presence of the polymer selected to form the skeleton of the final product. If the monomer/skeleton couple and the operating conditions are carefully chosen, then a transfer reaction may take place between the growing macroradical and the skeleton. This reaction generates a radical on the skeleton, and it is from this radical that the graft grows. The primary radical derived from the initiator may also contribute toward the transfer reactions.

As regards the copolymerization, this involves the grafting in a first stage, onto the end of the future pendent segment, of a free-radical-polymerizable function. This grafting may be performed via common methods of organic chemistry. Next, in a second stage, the macromonomer thus obtained is polymerized with the monomer chosen to form the skeleton and a "comb" polymer is obtained.

Among the hydrophobic monomers from which the hydrophobic block(s) of the amphiphilic polymer may be prepared, mention may be made especially of:
  linear, branched, cyclic or aromatic monocarboxylic or polycarboxylic acid esters, comprising at least one ethylenic unsaturation, saturated carboxylic acid esters containing 8 to 30 carbon atoms, optionally bearing a hydroxyl group;

α,β-ethylenically unsaturated nitriles, vinyl ethers, vinyl esters, vinylaromatic monomers, vinyl halides or vinylidene halides, linear or branched, aromatic or nonaromatic hydrocarbon-based monomers comprising at least one ethylenic unsaturation, monomers of cyclic or noncyclic siloxane type, and chlorosilanes;

propylene oxide or butylene oxide;

alone or as mixtures, and also macromonomers derived from such monomers.

As particular examples of hydrophobic monomers that may be included in the preparation of the hydrophobic block(s) of the amphiphilic block polymer, mention may be made of:

(meth)acrylic acid esters with an alcohol containing 1 to 12 carbon atoms, for instance methyl (meth)acrylate, ethyl (meth)acrylate, propyl (meth)acrylate, n-butyl (meth)acrylate, t-butyl (meth)acrylate, isobutyl (meth)acrylate or 2-ethylhexyl acrylate;

vinyl acetate, vinyl Versatate®, vinyl propionate, vinyl chloride, vinylidene chloride, methyl vinyl ether or ethyl vinyl ether;

vinyl nitriles, more particularly including those containing from 3 to 12 carbon atoms, in particular such as acrylonitrile and methyacrylonitrile;

styrene, α-methylstyrene, vinyltoluene, butadiene or chloroprene;

alone or as blends, and also macromonomers derived from such monomers.

The preferred monomers are acrylic acid esters with linear or branched $C_1$-$C_4$ alcohols, such as methyl, ethyl, propyl or butyl acrylate, vinyl esters, for instance vinyl acetate, styrene and α-methyl-styrene.

As regards the nonionic hydrophilic monomers from which the amphiphilic block polymers may be obtained, mention may be made, without wishing to be limited thereto, of ethylene oxide; linear, branched, cyclic or aromatic monocarboxylic or polycarboxylic acid amides comprising at least one ethylenic unsaturation, or derivatives, for instance (meth)acrylamide or N-methylol(meth)acrylamide; hydrophilic esters derived from (meth)acrylic acid, for instance 2-hydroxyethyl (meth)acrylate; vinyl esters for obtaining polyvinyl alcohol blocks after hydrolysis, for instance vinyl acetate, vinyl Versatate® or vinyl propionate. These monomers may be used alone, in combination, and also in the form of macromonomers. It is recalled that the term "macromonomer" denotes a macromolecule bearing one or more functions that may be polymerized via the method used.

However, the preferred hydrophilic monomers are acrylamide and methacrylamide, alone or as a blend, or in the form of macromonomers.

As regards the anionic hydrophilic monomers from which the amphiphilic block polymers may be obtained, mention may be made, for example, of monomers comprising at least one carboxylic, sulfonic, sulfuric, phosphonic, phosphoric or sulfosuccinic function, or the corresponding salts.

It is pointed out that under the pH conditions at which the amphiphilic block polymer is used, the functions of the anionic block(s) of the polymer are in an at least partially ionized (dissociated) form. More particularly, at least 10 mol % of the functions of the block(s) are in ionized form. The determination of this value poses no problem for a person skilled in the art; it especially depends on the pKa of the ionizable functions of the units of the polymer and on the number of these functions (i.e. the number of moles of monomers bearing ionizable functions used during the preparation of the polymer).

More particularly, the monomers are chosen from:

linear, branched, cyclic or aromatic monocarboxylic or polycarboxylic acids, N-substituted derivatives of such acids; polycarboxylic acid monoesters comprising at least one ethylenic unsaturation;

linear, branched, cyclic or aromatic vinyl-carboxylic acids;

amino acids comprising one or more ethylenic unsaturations;

alone or as blends, precursors thereof, sulfonic or phosphonic derivatives thereof, and also macromonomers derived from such monomers; the monomers or macromonomers possibly being in the form of salts.

Examples of anionic monomers that may be mentioned, without wishing to be limited thereto, include:

acrylic acid, methacrylic acid, fumaric acid, itaconic acid, citraconic acid, maleic acid, acrylamidoglycolic acid, 2-propene-1-sulfonic acid, methallylsulfonic acid, styrenesulfonic acid, α-acrylamidomethylpropanesulfonic acid, 2-sulfoethylene methacrylate, sulfopropylacrylic acid, bis(sulfopropyl)acrylic acid, bis(sulfo-propyl) methacrylic acid, sulfatoethylmethacrylic acid, hydroxyethylmethacrylic acid phosphate monoester, and also the alkali metal salts, for instance the sodium or potassium salt, or the ammonium salts;

vinylsulfonic acid, vinylbenzenesulfonic acid, vinylphosphonic acid, vinylidenephosphoric acid, vinylbenzoic acid, and also the alkali metal salts, for instance the sodium or potassium salts, or the ammonium salts;

N-methacryloylalanine or N-acryloylhydroxyglycine;

alone or as blends, and also macromonomers derived from such monomers.

It would not constitute a departure from the context of the present invention to use monomers which are precursors of those that have just been mentioned. In other words, these monomers contain units that, once incorporated into the polymer chain, may be converted, especially via a chemical treatment such as hydrolysis, to regenerate the abovementioned anionic species. For example, the totally or partially esterified monomers of the abovementioned monomers may be used in order thereafter to be totally or partially hydrolyzed.

As cationic hydrophilic monomers from which the amphiphilic block polymers may be obtained, mention may be made especially of:

aminoalkyl (meth)acrylates and aminoalkyl (meth)acrylamides;

monomers comprising at least one secondary, tertiary or quaternary amine function, or a heterocyclic group containing a nitrogen atom, vinylamine or ethyleneimine;

diallyldialkylammonium salts;

alone or as mixtures, or the corresponding salts, and also macromonomers derived from such monomers.

Said monomers may contain a counterion chosen from halides, for instance chlorine, sulfates, hydrosulfates, alkyl sulfates (for example containing 1 to 6 carbon atoms), phosphates, citrates, formates and acetates.

As examples of cationic monomers that are suitable, the following monomers, inter alia, are given:

dimethylaminoethyl (meth)acrylate, dimethylamino-propyl (meth)acrylate, di-tert-butylaminoethyl (meth) acrylate, dimethylaminomethyl(meth)-acrylamide and dimethylaminopropyl(meth)-acrylamide;

ethyleneimine, vinylamine, 2-vinylpyridine and 4-vinylpyridine;

trimethylammoniumethyl (meth)acrylate chloride, trimethylammoniumethyl acrylate methyl sulfate, benzyldimethylammoniumethyl (meth)acrylate chloride, 4-benzoylbenzyldimethylammoniumethyl acrylate chloride, trimethylammoniumethyl (meth)-acrylamide chloride and vinylbenzyltrimethyl-ammonium chloride;

diallyldimethylammonium chloride;

alone or as blends, or the corresponding salts thereof, and also macromonomers derived from such monomers.

Preferably, the block amphiphilic polymers have a weight-average molar mass of less than or equal to 100 000 g/mol, more particularly between 1000 and 50 000 g/mol and preferably between 1000 and 20 000 g/mol. It is pointed out that the weight-average molar masses indicated above are theoretical molar masses, evaluated as a function of the respective amounts of monomers introduced during the preparation of said polymers.

Preferably, an amphiphilic block polymer of nonionic type is used.

As examples of amphiphilic block polymers that are suitable for use in the invention, mention may be made of polyhydroxystearate-polyethylene glycol-polyhydroxystearate triblock polymers (the products of the Arlacel range from ICI are an example thereof) and polymers containing polyalkylpolyether-grafted poly-dimethylsiloxane blocks (for instance the products of the Tegopren brand name sold by Goldschmidt).

According to a second variant, at least one cationic surfactant is used as inner surfactant. In the case of this second variant, the inner surfactant does not satisfy Bancroft's rule mentioned previously. Specifically, the cationic surfactant is soluble in the dispersed phase rather than in the continuous phase of the inverse emulsion.

Among the suitable cationic surfactants that may especially be used are aliphatic or aromatic fatty amines, aliphatic fatty amides and quaternary ammonium derivatives (Rhodoquat RP50 from Rhodia Chimie).

Finally, a third variant of the invention consists in combining the two possibilities that have just been detailed.

Irrespective of the variant adopted, the total content of inner surfactant and/or inner amphiphilic polymer more particularly represents from 0.1% to 10% by weight and preferably from 2% to 10% by weight relative to the inner aqueous phase.

According to one particularly advantageous embodiment, the inverse emulsion comprises an amphiphilic polymer or a blend of several such polymers.

Moreover, the inner aqueous phase/inner organic phase weight ratio is more particularly between 30/70 and 90/10 and preferably between 50/50 and 90/10.

As regards the outer aqueous phase of the multiple emulsion, this may optionally comprise at least one hydrophilic active material. Everything that has been mentioned during the description of the hydrophilic materials that may be included in the composition of the inner aqueous phase remains valid in the present case and reference may thus be made thereto.

If the outer aqueous phase comprises one or more active materials, their total content is more particularly between 0.1% and 50% by weight of the outer aqueous phase and preferably between 0.1% and 20% by weight of the outer aqueous phase.

The outer aqueous phase may similarly comprise additional adjuvants, for instance preserving agents.

The outer aqueous phase furthermore comprises at least one outer surfactant and/or at least one outer amphiphilic polymer.

More particularly, the surfactants and polymers satisfy Bancroft's rule and are preferably chosen from the compounds that satisfy the following two conditions:

when they are mixed with the outer aqueous phase (i.e. the continuous phase of the multiple emulsion), at a concentration of between 0.1% and 10% by weight of said phase and between 20 and 30° C., they are in the form of a solution in all or part of the indicated concentration range, when they are mixed with the inner organic phase (i.e. the dispersed phase of the multiple emulsion), at a concentration of between 0.1% and 10% by weight of said phase and between 20 and 30° C., they are in the form of a dispersion in all or part of the indicated concentration range.

According to a first variant, the outer surfactant and/or outer amphiphilic polymer are chosen from nonionic surfactants and nonionic amphiphilic polymers, optionally combined with at least one anionic surfactant and/or at least one anionic amphiphilic polymer.

According to this first variant, the total content of outer surfactant(s) and/or outer amphiphilic polymer(s) is between 0.5% and 10% by weight and preferably between 1% and 5% by weight relative to the inverse emulsion; the amount of anionic surfactant(s) and/or anionic amphiphilic polymer(s), if they are present, represents 0.5% to 5% by weight and preferably 0.5% to 2% by weight relative to the weight of nonionic surfactant(s) and/or nonionic amphiphilic polymer(s).

As regards the nonionic surfactants, polyalkoxylated nonionic surfactants are preferably used.

Advantageously, the polyalkoxylated nonionic surfactant is chosen from the following surfactants, alone or as a mixture:

alkoxylated fatty alcohols
alkoxylated mono-, di- and triglycerides
alkoxylated fatty acids
alkoxylated sorbitan esters
alkoxylated fatty amines
alkoxylated bis(1-phenylethyl)phenols
alkoxylated tris(1-phenylethyl)phenols
alkoxylated alkylphenols the number of alkoxylated units, more particularly ethoxylated and/or propoxylated units, is such that the HLB value is greater than or equal to 10.

The surfactants mentioned as being suitable for the inverse emulsion may be taken, except for the fact that the number of ethoxylated and propoxylated units should be adapted as a function of the desired HLB value. For purely illustrative purposes, the total number of ethoxylated units and optionally propoxylated units is between 10 and 100.

As regards the nonionic amphiphilic polymers that are suitable, and in accordance with a first embodiment, these polymers are polyalkoxylated compounds comprising at least two blocks, one of them being hydrophilic, the other hydrophobic; at least one of the blocks comprising polyalkoxylated units, more particularly polyethoxylated and/or polypropoxylated units.

That which has been stated previously in the context of the description of the nonionic hydrophilic monomers and of the hydrophobic monomers that may be used for the preparation of the amphiphilic block polymers included in the composition of the inverse emulsion remains valid and will not be repeated here.

For purely indicative purposes, said amphiphilic polymers are preferably obtained by performing ring-opening polymerizations, especially anionic polymerizations.

More particularly, said nonionic polyalkoxylated amphiphilic polymers are chosen from polymers whose weight-average molar mass is less than or equal to 100 000 g/mol (measured by GPC, polyethylene glycol standard), preferably of between 1000 and 50 000 g/mol and preferentially between 1000 and 20 000 g/mol.

Examples of polymers of this type that may be mentioned, inter alia, include polyethylene glycol/polypropylene glycol/polyethylene glycol triblock polymers. Such polymers are well known and are especially sold under the brand names Pluronic (sold by BASF) and Arlatone (sold by ICI).

According to another embodiment, the nonionic amphiphilic polymer is an amphiphilic block polymer obtained by polymerization of at least one nonionic hydrophilic monomer and of at least one hydrophobic monomer, the proportion and nature of said monomers being such that the resulting polymer satisfies the conditions mentioned previously (Bancroft's rule—two conditions).

These amphiphilic polymers furthermore comprise at least one hydrophobic block and at least one neutral (nonionic) hydrophilic block.

In the case where said polymer comprises at least three blocks, and more particularly three blocks, the polymer is advantageously linear. In addition, the hydrophilic blocks are more particularly located at the ends.

In the case where the polymers comprise more than three blocks, these blocks are preferably in the form of grafted or comb polymers.

The lists of nonionic hydrophilic monomers and of hydrophobic monomers, and also the various preparation methods, cited in the context of the description of the amphiphilic block polymers, may be repeated in the case of the polymers according to this second variant.

However, the preferred hydrophilic monomers are acrylamide and methacrylamide, alone or as a mixture, or in the form of macromonomers; the preferred monomers are acrylic acid esters with linear or branched $C_1$-$C_4$ alcohols, such as methyl acrylate, ethyl acrylate, propyl acrylate and butyl acrylate, and vinyl esters, for instance vinyl acetate, styrene and α-methylstyrene.

In the case where the nonionic surfactant and/or nonionic amphiphilic polymer are combined with at least one anionic surfactant and/or anionic amphiphilic polymer, among the suitable anionic surfactants that may be mentioned, alone or as mixtures, are:

alkyl ester sulfonates, for example of formula R—CH(SO$_3$M)-COOR', in which R represents a $C_8$-$C_{20}$ and preferably $C_{10}$-$C_{16}$ alkyl radical, R' represents a $C_1$-$C_6$ and preferably $C_1$-$C_3$ alkyl radical and M represents an alkali metal cation (sodium, potassium or lithium), substituted or unsubstituted ammonium (methyl-, dimethyl-, trimethyl- or tetramethylammonium, dimethylpiperidinium, etc.) or an alkanolamine derivative (monoethanolamine, diethanolamine, triethanolamine, etc.). Mention may be made most particularly of methyl ester sulfonates in which the radical R is of $C_{14}$-$C_{16}$;

alkyl benzene-sulfonates, more particularly of $C_9$-$C_{20}$, primary or secondary alkyl sulfonates, especially of $C_8$-$C_{22}$, alkylglyceryl sulfonates, sulfonated polycarboxylic acids, for instance those described in GB 1 082 179, and paraffin sulfonates;

alkyl sulfates, for example of formula ROSO$_3$M, in which R represents a $C_{10}$-$C_{24}$ and preferably $C_{12}$-$C_{20}$ alkyl or hydroxyalkyl radical; M representing a hydrogen atom or a cation of the same definition as above, and also the polyalkoxylated (ethoxylated (EO), propoxylated (PO), or combinations thereof) derivatives thereof, for instance sodium dodecyl sulfate;

alkyl ether sulfates, for example of formula RO(CH$_2$CH$_2$O)$_n$SO$_3$M in which R represents a $C_{10}$-$C_{24}$ and preferably $C_{12}$-$C_{20}$ alkyl or hydroxyalkyl radical; M representing a hydrogen atom or a cation of the same definition as above, n generally ranging from 1 to 4, and also the polyalkoxylated (ethoxylated (EO), propoxylated (PO), or combinations thereof) derivatives thereof, for instance lauryl ether sulfate with n=2;

alkylamide sulfates, for example of formula RCONHR'OSO$_3$M in which R represents a $C_2$-$C_{22}$ and preferably $C_6$-$C_{20}$ alkyl radical, R' represents a $C_2$-$C_3$ alkyl radical, M representing a hydrogen atom or a cation of the same definition as above, and also the polyalkoxylated (ethoxylated (EO), propoxylated (PO), or combinations thereof) derivatives thereof;

saturated or unsaturated fatty acid salts, for instance those of $C_8$-$C_{24}$ and preferably of $C_{14}$-$C_{20}$, N-acyl N-alkyltaurates, alkyl isethionates, alkyl succinamates and alkyl sulfosuccinates, sulfo-succinate monoesters or diesters, N-acyl sarcosinates and polyethoxycarboxylates; and alkyl and/or alkyl ether and/or alkylaryl ether ester phosphates.

Among the anionic polymers that may be used, mention may be made most particularly of block, preferably diblock or triblock, polymers obtained by polymerization of at least one anionic hydrophilic monomer, optionally of at least one nonionic hydrophilic monomer, and of at least one hydrophobic monomer.

In this case also, the choice of monomers and the respective proportions thereof are such that the resulting polymer satisfies the two conditions mentioned above (Bancroft's rule).

The nonionic and anionic hydrophilic monomers, the hydrophobic monomers and the synthesis methods cited in the context of the description of the inner amphiphilic polymers may be used to obtain the outer amphiphilic polymers according to this variant. Reference may thus be made thereto.

A second variant of the invention consists in using as outer surfactant and/or outer amphiphilic polymer at least one anionic amphiphilic polymer optionally combined with at least one anionic surfactant; the total content of anionic amphiphilic polymers and/or anionic surfactants is between 0.5% and 10% by weight and preferably between 1% and 5% by weight relative to the inverse emulsion.

Reference may be made to the lists indicated for the first variant of outer surfactants and/or outer polymers as regards the surfactants and/or polymers in accordance with this variant.

In addition, the outer aqueous phase may comprise at least one additive, one of the roles of which is to equilibrate the osmotic pressures of the outer aqueous phase and of the inner aqueous phase. Among the additives that may be envisioned, mention may be made of salts chosen from alkali metal or alkaline-earth metal halides (for instance sodium chloride or calcium chloride), at least one alkali metal or alkaline-earth metal sulfate (for instance sodium sulfate) or mixtures thereof; sugars (for example glucose) or polysaccharides (especially dextran) or mixtures thereof. The outer aqueous phase may comprise a combination of all these additives.

The salt, sugar and/or polysaccharide concentrations are such that the osmotic pressures of the outer and inner aqueous phases are equilibrated.

According to one particular embodiment of the invention, the outer aqueous phase comprises at least one water-soluble or water-dispersible compound, as additive for drying the multiple emulsion. Specifically, in the presence of these compounds, it becomes possible to dry the multiple emulsion (in other words to remove the outer water from said emulsion) in order to obtain granules.

According to a first possibility, said compound is chosen from the polymers obtained by polymerization of at least one aliphatic, cyclic or aromatic, linear or branched, ethylenically unsaturated monocarboxylic or polycarboxylic acid or anhydride monomer (I) and of at least one linear or branched, monoethylenically or polyethylenically unsaturated hydrocarbon-based monomer (II), and/or of at least one ethylenically unsaturated polyalkoxylated carboxylic acid ester monomer (III).

Preferably, said compound is chosen from the polymers obtained by polymerization of at least one monomer (I) and of at least one monomer (II). More particularly, said polymerization is a free-radical polymerization.

According to one advantageous embodiment, the monomer (I) has the following formula: $(R^1)(R^1)-C=C(R'^1)-COOH$; in which formula the radicals $R^1$ and $R'^1$, which may be identical or different, represent a hydrogen atom, a $C_1$-$C_{10}$ hydrocarbon-based radical optionally comprising a —COOH group, or a —COOH group. Preferably, one of the radicals $R^1$ represents a hydrogen atom and the other radical $R^1$ represents a hydrogen atom, a —COOH or —(CH$_2$)—COOH group or a methyl radical, and $R'^1$ represents a hydrogen atom, a —CH$_2$—COOH group or a methyl radical.

The monomer of formula (I) is advantageously chosen from acrylic, methacrylic, citraconic, maleic, fumaric, itaconic and crotonic acids or anhydrides.

As regards the monomer of formula (II), it more especially corresponds to the following formula: $(R^2)(R^2)-C=CH_2$; in which the radicals $R^2$, which may be identical or different, represent a linear or branched $C_1$-$C_{10}$ hydrocarbon-based radical. More particularly, said radicals are alkyl or alkenyl radicals, the latter radicals possibly comprising one or more ethylenic unsaturations. Preferably, said radicals do not comprise any hetero atoms.

This monomer may be chosen especially from ethylene, propylene, 1-butene, isobutylene, n-1-pentene, 2-methyl-1-butene, n-1-hexene, 2-methyl-1-pentene, 4-methyl-1-pentene, 2-ethyl-1-butene, diisobutylene (or 2,4,4-trimethyl-1-pentene) and 2-methyl-3,3-dimethyl-1-pentene.

The water-soluble or water-dispersible compound may similarly be chosen from the polymers derived from the polymerization of at least one monomer (I); from polypeptides of natural or synthetic origin, or alternatively from depolymerized polysaccharides obtained, for example, from dextran, starch, maltodextrin, xanthan gum and galactomannans (guar or carob) and preferably having a melting point of greater than 100° C. and a solubility in water of between 50 and 500 g/l. Said polymers may optionally comprise at least one saturated or unsaturated, aromatic or nonaromatic $C_4$-$C_{30}$ hydrocarbon-based hydrophobic graft, optionally interrupted with one or more hetero atoms.

It should be noted that the grafts are linked to the skeleton of the polymer via amide, ester, urea, urethane, isocyanate or amino bonds depending on the nature of the reactive functions of the polymer to be grafted, for example carboxylic acid, amine, alcohol, etc. functions.

Preferably, the weight-average molar mass of such polymers, whether or not they are grafted, is less than or equal to 20 000 g/mol (absolute masses, measured by MALLS (multiangle laser light scattering) coupled to gel permeation chromatography).

If one or more water-soluble or water-dispersible compounds is (are) present, their total content in the outer aqueous phase is preferably such that the content of this compound in the dried multiple emulsion (i.e. in the final granule) is between 30% and 70% by weight of the dried multiple emulsion.

It is pointed out that in the case where such a water-soluble or water-dispersible compound is present, the outer surfactants and/or outer polymers are preferably chosen from nonionic surfactants and/or nonionic amphiphilic polymers of polyalkoxylated type.

According to one variant of the present invention, the outer aqueous phase may comprise a dispersed outer organic phase and/or a dispersed solid.

Everything that has been stated previously regarding the hydrophobic active material optionally present in the inner organic phase remains valid and will not be detailed again now.

In the case where such an outer organic phase is present, it more particularly represents 1% to 50% by weight of the outer aqueous phase and preferably 5% to 25% by weight of the outer aqueous phase.

In addition, it is preferable for the size of the droplets of the outer organic phase to be at most of the same order of magnitude as that of the inverse emulsion dispersed in the outer aqueous phase.

As regards the possibility of using a solid dispersed in the outer aqueous phase, any solid used in the various applications mentioned may be suitable. Preferably, the size of this dispersed solid is in the region of or smaller than that of the droplets of the inverse emulsion.

In the case where the dispersed solid is present, its content more particularly ranges from 1% to 50% by weight and preferably from 5% to 25% by weight of the outer aqueous phase.

According to one embodiment of the invention, the multiple emulsions are concentrated. More specifically, in the concentrated multiple emulsion, the inverse emulsion/outer aqueous phase weight ratio is between 50/50 and 90/10 and preferably between 70/30 and 90/10.

According to another possibility of the invention, these concentrated multiple emulsions may be diluted.

One of the first advantages of such a dilution step is that the viscosity of the multiple emulsions can be adapted. Specifically, in certain cases, it is preferable to have available pourable multiple emulsions.

Another advantage of preparing more dilute multiple emulsions is that additives such as preserving agents can be introduced at this stage of the dilution, and also thickeners, the main effect of which is to prevent creaming and/or sedimentation of the dilute multiple emulsion.

Among the thickening polymers that are suitable, those extracted from plants and optionally modified, such as carrageenans, alginates, carboxy-methylcelluloses, methylcelluloses, hydroxypropyl-celluloses and hydroxyethylcelluloses, may be used.

It is similarly possible to use thickening polymers of the type such as polysaccharides of animal, plant or bacterial origin, especially such as xanthan gum, guar and derivatives (for instance hydroxypropyl guar) and polydextroses, or combinations thereof.

When it is present, the content of thickening polymer is more particularly between 0.1% and 2% by weight relative to the aqueous phase in the dilute multiple emulsion (outer aqueous phase and aqueous dilution phase) and preferably between 0.1% and 0.5% by weight relative to the aqueous phase in the dilute multiple emulsion. It is pointed out that in this concentration range, the thickening polymer is soluble in the aqueous phase.

The process according to the invention thus consists in performing the following steps:
a) the inverse emulsion is prepared;
b) the outer aqueous phase is prepared;
c) the outer aqueous phase is introduced into the inverse emulsion, without stirring;
d) the mixture is stirred;
e) the concentrated multiple emulsion thus obtained is optionally diluted by adding, with stirring, an aqueous dilution phase comprising at least one outer surfactant and/or at least one outer amphiphilic polymer, in order to obtain a dilute multiple emulsion.

Step a) of the process according to the invention, which consists in preparing the inverse emulsion, may be performed using standard methods.

Thus, to give but one example, a first mixture comprising water, the hydrophilic active material, optionally the additive (salt, sugar, polysaccharide) and optionally at least one cationic surfactant, if it is present, is prepared on the one hand, and a second mixture comprising the compound used as organic phase, optionally the inner surfactant(s) and/or the inner amphiphilic polymer(s), and optionally the hydrophobic active material, is prepared on the other hand. The first mixture is then added to the second, with stirring.

In the case where the organic phase is of low viscosity (dynamic viscosity of less than 1 Pa.s, measured using a Brookfield viscometer according to AFNOR standard NFT 76 102 of February 1972), the stirring is preferably vigorous and may advantageously be performed using a machine such as an Ultra-Turrax® homogenizer, a Microfluidizer or any high-pressure homogenizer.

In the case where the organic phase is viscous (dynamic viscosity of greater than or equal to 1 Pa.s; Brookfield; AFNOR standard NFT 76 102 of February 1972), the stirring may advantageously be performed using a frame paddle, a planetary mixer, a mixer with a scraping rotor and a counter-rotating paddle (counter-stirring).

The preparation of the inverse emulsion is generally performed at a temperature above the melting point of the compound used as organic phase, but below the degradation temperature of the components included in the composition of the inverse emulsion. More particularly, this temperature is between 20 and 80° C.

The stirring time may be determined without difficulty by a person skilled in the art, and depends on the type of apparatus used. It is preferably sufficient to obtain a mean droplet size of the inverse emulsion of between 0.1 and 10 μm and preferably between 0.1 and 1 μm. The mean droplet size corresponds to the median volumetric diameter (d50), which represents the diameter of the particle equal to 50% of the cumulative distribution, and may be measured either with a Horiba granulometer or with an optical microscope.

Step b) of the process according to the invention consists in preparing the outer aqueous phase. This is obtained by mixing water, the outer surfactant(s) and/or outer amphiphilic polymers, optionally one or more hydrophilic active materials, optionally at least one additive (salt, sugar) and, where appropriate, the water-soluble or water-dispersible compound.

According to one advantageous embodiment of the invention, and in the case where a dilution step e) is performed, the additive is introduced only at this dilution stage.

In the case where the water-soluble or water-dispersible compound is present, a first variant consists in first mixing together all the abovementioned constituent components, except for said compound, so as to introduce it only once into the mixture obtained above.

According to another variant, which is preferred, if the water-soluble or water-dispersible compound is present, it is introduced only at the stage of the dilution step e) or after this stage.

It is pointed out that said outer aqueous phase may also comprise adjuvants such as preserving agents.

The preparation of the outer aqueous phase may be performed at room temperature. However, it may be advantageous to prepare the outer aqueous phase at a temperature in the region of that at which the inverse emulsion is prepared.

Once the outer aqueous phase has been obtained, it is added to the inverse emulsion, during step c), without stirring.

Next, after all of the outer aqueous phase has been introduced into the inverse emulsion, the mixture is stirred.

Advantageously, the stirring is performed using medium-shear blenders such as, for example, stirrers equipped with frame paddles, planetary blenders or blenders containing a scraping rotor and a counter-rotating paddle (counter-stirring)

This stirring operation preferably takes place at a temperature at which the compound constituting the inner organic phase is in a liquid form (temperature above the melting point of the compound constituting the inner organic phase) and is more particularly between 20 and 80° C.

It should be noted that, depending on the nature of the active material(s) of the multiple emulsion, or of some of the constituent components of said emulsion, especially such as the water-soluble or water-dispersible compound, it may be advantageous to adjust the pH of the outer aqueous phase by adding a base (sodium hydroxide or potassium hydroxide) or an acid (hydrochloric acid).

For illustrative purposes, the usual pH range of the outer aqueous phase is between 3 and 8 and preferably between 5 and 8.

After this stirring step d), a concentrated multiple emulsion whose inverse emulsion/outer aqueous phase weight ratio is between 50/50 and 90/10 and preferably between 70/30 and 90/10 is obtained.

Depending on the applications, an optional additional dilution step may be envisioned.

Such a step may be advantageous, for example when it is desired to add additional compounds to the multiple emulsion, especially such as compounds that may be used to dry the multiple emulsion, and/or various additives such as thickeners, preserving agents, and/or an organic phase dispersed in the outer aqueous phase, and/or alternatively a solid phase dispersed in this same phase.

This dilution step is performed by adding, with stirring, an aqueous dilution phase comprising at least one outer surfactant and/or at least one outer amphiphilic polymer, which are preferably the same as those present in the outer phase of the concentrated multiple emulsion.

Preferably, the amount of outer surfactant and/or of outer amphiphilic polymer in the aqueous dilution phase is such that the amount of outer surfactant and/or of outer amphiphilic polymer is between 1% and 10% by weight relative to the outer aqueous phase of the dilute multiple emulsion (i.e. of the combination of aqueous dilution phase and outer aqueous phase of the concentrated multiple emulsion). Preferably, this content is between 1% and 5% by weight of the outer aqueous phase of the dilute multiple emulsion.

It should be noted that the amount of dilution water is advantageously such that the inverse emulsion/outer aqueous phase weight ratio of the dilute multiple emulsion is between 10/90 and 50/50. Thus, for example, a concentrated multiple emulsion with an inverse emulsion/outer aqueous phase weight ratio of 90/10 may be diluted until a weight ratio of 50/50 or even 10/90 is obtained. A concentrated multiple emulsion with an inverse emulsion/outer aqueous phase weight ratio of 50/50 may be diluted until a weight ratio of 10/90 is obtained.

In addition, the aqueous dilution phase may comprise, if necessary, at least one additive (salt, sugar and/or polysaccharide) in an amount such that the osmotic pressure of the outer aqueous phase of the dilute multiple emulsion (outer aqueous phase of the concentrated multiple emulsion and aqueous dilution phase) is equilibrated with that of the inner aqueous phase.

The stirring during the dilution step is preferably performed using medium-shear blenders of the type used during step d).

As mentioned previously, in the case where it is desired to incorporate a water-soluble or water-dispersible compound into the multiple emulsion, this may be performed either with the dilution water to be added, or after the multiple emulsion has been diluted, working in such a way that the content of water added with said water-soluble or water-dispersible compound, calculated as a function of the amount of water added to make the dilute multiple emulsion, is such that the weight ratio of inverse emulsion/outer aqueous phase of the final (dilute) multiple emulsion is within the ranges indicated previously.

According to a second variant, the aqueous dilution phase comprises a dispersed outer organic phase comprising a hydrophobic active material.

In this case, a direct emulsion comprising the outer organic phase comprising the hydrophobic active material, and the outer aqueous dilution phase comprising the outer surfactant(s) and/or the outer amphiphilic polymer(s) is prepared. Next, the direct emulsion is added to the concentrated multiple emulsion obtained previously. Obviously, the amounts of outer aqueous dilution phase with the inverse and direct emulsions are such that the weight proportions of each of the phases satisfy the conditions explained above for the multiple emulsion after dilution. Preferably, the outer surfactants and/or outer amphiphilic polymers are the same as those of the outer aqueous phase of the concentrated multiple emulsion.

The direct emulsion is obtained according to any known method, by mixing with stirring of the two phases: the outer organic phase comprising the hydrophobic active material and the outer aqueous phase comprising the outer surfactant and/or outer amphiphilic polymer.

In the case where the outer aqueous phase comprises a dispersed solid, the multiple emulsion may be obtained as indicated in the first case, followed by adding said dispersed solid either with the outer aqueous dilution phase or after the addition of said outer aqueous dilution phase.

The mean droplet size of the multiple emulsion advantageously ranges between 5 and 100 μm, more particularly between 5 and 50 μm and advantageously between 10 and 15 μm. The mean droplet size, corresponding to the median volumetric diameter (d50), which represents the diameter of the particle equal to 50% of the cumulative distribution, is measured using a Horiba machine and/or with an optical microscope.

In the case where a water-soluble or water-dispersible compound is present, the multiple emulsion is then dried so as to obtain granules.

The drying operation (consisting in removing the water from the outer aqueous phase) may be performed by any means known to those skilled in the art.

Preferably, the drying is performed such that at least 90% by weight of the outer aqueous phase and preferably between 90% and 95% by weight is removed.

By performing the drying under such conditions, the granules dried according to the present invention comprise an inner water content of between 10% and 50% by weight of the granule and preferably between 20% and 30% by weight of the granule.

Thus, according to a first embodiment of the invention, oven-drying may be envisioned. Preferably, this drying takes place in a thin layer.

Usually, the drying temperature is less than or equal to 100° C. More particularly, temperatures of between 50 and 90° C. are suitable for performing this method.

According to another embodiment, a method of fast-drying of the multiple emulsion is used. Spray-drying or drying using Duprat® drums, or alternatively freeze-drying (freezing-sublimation) are suitable in this respect. Spray-drying may be performed in a usual manner in any known apparatus, for instance a spraying tower combining spraying performed with a nozzle or a turbomixer with a stream of hot gas.

The gas inlet temperature is from about 100° C. to 120° C. and the outlet temperature of the spraying gases is preferably between 55 and 70° C. These temperatures are given as a guide, and depend on the heat stability of the various components. Furthermore, it is defined according to the final water content desired in the granule.

In the case of multiple-emulsion drying operations performed using a Duprat® drum or using means for rapidly obtaining a dry film that is separated from the drying support by means of a scraping operation, for example, granules are obtained, which may optionally be ground. If necessary, these granules may undergo subsequent processing, for instance an aggregation step, so as to obtain aggregated granules.

It should be noted that additives, such as anticaking agents or fillers (for instance silica, kaolin, titanium dioxide, etc.) may be incorporated into the granules.

These additives may be introduced before drying the multiple emulsion, as may be the case especially for fillers. They may also be co-dried with the multiple emulsion, as is especially the case for the anticaking agents.

Advantageously, the mean size (d50) of the granules obtained directly after drying is between 100 μm and a few millimeters (Sympatec) and preferably between 100 and 800 μm.

A concrete but nonlimiting example of the invention will now be given.

EXAMPLE

1/Inverse Emulsion

Composition of the Inverse Emulsion:
* 80% of inner aqueous phase comprising a mixture of:
   6.25% of a lactic acid solution (% by weight of 0.1M solution expressed relative to the weight of aqueous phase)
   93.75% of an NaCl solution (% by weight of 0.1M solution expressed relative to the weight of aqueous phase)
* 20% of oil phase (Primol 352 oil (*) and surfactant) comprising 5% surfactant (Tegopren 7008 (**); % expressed by weight relative to the weight of inner aqueous phase)
(*) Primol 352 oil: medicinal white liquid petroleum jelly, sold by ESSO SAF
(**) Tegopren 7008: alkyl- and polyether-modified polymethylsiloxane; sold by Goldschmidt Preparation of the Inverse Emulsion The Primol oil and the surfactant are introduced into a 10 liter Trimix reactor (Rayneri) equipped with a doctor blade, counter-stirring and a rotor-stator, and the mixture is then stirred at room temperature.

The aqueous phase is then introduced, over 80 minutes, with slow stirring (doctor blade—63 rpm; counter-stirring—190 rpm).

To refine the emulsion, the stirring is continued (doctor blade—63 rpm; counter-stirring—190 rpm and rotor-stator at 1000 rpm) for 20 minutes.

A viscous inverse emulsion with a particle size of less than one micron (observation made by optical microscopy) is obtained.

2/Concentrated Multiple Emulsion

Composition of the Multiple Emulsion
* 90% inverse emulsion
* 10% outer aqueous phase containing:
   10% Arlatone F127G (*) (ICI-Uniquema; % by weight expressed relative to the weight of outer aqueous phase of the concentrated multiple emulsion).
(*) Arlatone F127G:

Preparation of the Concentrated Multiple Emulsion

The outer aqueous phase is added, quickly and without stirring, to the inverse emulsion obtained beforehand.

The mixture is then stirred (doctor blade at 63 rpm and counter-stirring at 190 rpm).

A concentrated multiple emulsion with a mean droplet size (d50) in the region of 10 µm and a low polydispersity index is obtained.

3/Dilute Multiple Emulsion

Composition of the Dilute Multiple Emulsion
* 50% inverse emulsion
* 50% outer aqueous phase containing:
   2% Arlatone F127G (% by weight expressed relative to the weight of the inverse emulsion);
   3.2% glucose (% by weight expressed relative to the weight of outer aqueous phase of the dilute multiple emulsion);
   1% Rhodopol 23 (*) (Rhodia Chimie; % by weight expressed relative to the weight of outer aqueous phase of the dilute multiple emulsion).
(*) Rhodopol 23: xanthan gum Preparation of the Dilute Multiple Emulsion Preparation of the Outer Aqueous Dilution Phase The outer aqueous phase is prepared in two stages.

Firstly, a first aqueous 2% solution of Rhodopol 23 is prepared.

A second solution comprising water, the ground Arlatone, the glucose and the preserving agent (formaldehyde) is prepared using a deflocculating paddle stirrer. It is pointed out that the content of added water takes into account the content of water added for the preparation of the concentrated multiple emulsion so as to obtain an inverse emulsion/total aqueous phase (outer aqueous phase and aqueous dilution phase) weight ratio of 50/50.

The two solutions thus prepared are then mixed together.

Preparation of the Multiple Emulsion:

The outer aqueous dilution phase prepared is introduced, over 10 minutes, into the concentrated multiple emulsion obtained above, at room temperature and with slow stirring (doctor blade at 63 rpm and counter-stirring at 190 rpm), and stirring is continued for 30 minutes after the end of introduction of the outer aqueous dilution phase.

A dilute multiple emulsion that has the same particle size (d50) as that of the concentrated multiple emulsion, i.e. 10 µm, is obtained.

The same example was repeated using a polybutene oil, Napvis D107, sold by BP Chemicals, and a dilute multiple emulsion of the same particle size is obtained.

The invention claimed is:

1. A process for preparing a multiple emulsion comprising an inverse emulsion consisting of an inner aqueous phase dispersed in an inner organic phase, the inverse emulsion being dispersed in an outer aqueous phase;
   the inner aqueous phase optionally comprising at least one hydrophilic active material;
   the inner organic phase optionally comprising at least one hydrophobic active material;
   the inverse emulsion comprising at least one inner surfactant and/or at least one inner amphiphilic polymer;
   the outer aqueous phase optionally comprising at least one hydrophilic active material and at least one outer surfactant or at least one outer amphiphilic polymer;
   said process comprising the following steps:
   a) preparing the inverse emulsion;
   b) preparing the outer aqueous phase;
   c) adding the outer aqueous phase into the inverse emulsion, without stirring;
   d) stirring the mixture to obtain a concentrated multiple emulsion; and
   e) optionally, diluting the concentrated multiple emulsion obtained in step d) by adding, with stirring, an aqueous dilution phase comprising at least one outer surfactant or at least one outer amphiphilic polymer, in order to obtain a dilute multiple emulsion.

2. The process as claimed in claim 1, wherein the multiple emulsion presents a inner aqueous phase/inner organic phase weight ratio of between 30/70 and 90/10.

3. The process as claimed in claim 2, wherein the ratio is between 50/50 and 90/10.

4. The process as claimed in claim 1, wherein the inner aqueous phase further comprises:

a salt which is an alkali metal halide, an alkaline-earth metal halide, a alkali metal sulfate, or an alkaline-earth metal sulfate, or a sugar, or a polysaccharide, or mixtures thereof.

5. The process as claimed in claim 4, wherein the salt presents a concentration in the inner aqueous phase of between 0.05 and 1 mol/l; the sugar or polysaccharide concentration is such that the osmotic pressure of the inner aqueous phase comprising the sugar or the polysaccharide corresponds to the osmotic pressure of an inner aqueous phase comprising 0.05 to 1 mol/l of salt.

6. The process as claimed in claim 5, wherein the concentration of the salt is of 0.1 to 0.4 mol/l.

7. The process as claimed in claim 1, wherein the inner surfactant(s) or the inner amphiphilic polymer(s) are nonionic surfactants or amphiphilic block polymers or cationic surfactants, the total content of inner surfactant(s) or inner amphiphilic polymer(s) representing from 0.1% to 10% by weight of the inner organic phase.

8. The process as claimed in claim 1, wherein the multiple emulsion presents an inverse emulsion/outer aqueous phase weight ratio in the concentrated multiple emulsion of between 50/50 and 90/10.

9. The process as claimed in claim 8, wherein the ratio is between 70/30 and 90/10.

10. The process as claimed in claim 1, wherein the outer aqueous phase comprises, as outer surfactant or outer amphiphilic polymer:

at least one nonionic surfactant and/or at least one nonionic amphiphilic polymer, optionally combined with at least one anionic surfactant or at least one anionic amphiphilic polymer; the total content of outer surfactant(s) or outer amphiphilic polymer(s) is between 0.5% and 10% by weight relative to the inverse emulsion; the amount of anionic surfactant(s) and/or anionic amphiphilic polymer(s), if they are present, represents 0.5% to 5% by weight by weight relative to the weight of nonionic surfactant(s) and/or nonionic amphiphilic polymer(s); or at least one anionic amphiphilic polymer optionally combined with at least one anionic surfactant; the total content of anionic amphiphilic polymer(s) and/or anionic surfactant(s) is between 0.5% and 10% by weight relative to the inverse emulsion.

11. The process as claimed in claim 10, wherein the outer aqueous phase comprises, as outer surfactant or outer amphiphilic polymer:

at least one nonionic surfactant or at least one nonionic amphiphilic polymer, optionally combined with at least one anionic surfactant or at least one anionic amphiphilic polymer; the total content of outer surfactant(s) and/or outer amphiphilic polymer(s) is between 1% and 5% by weight relative to the inverse emulsion; the amount of anionic surfactant(s) and/or anionic amphiphilic polymer(s), if they are present, represents 0.5% to 2% by weight relative to the weight of nonionic surfactant(s) or nonionic amphiphilic polymer(s); or at least one anionic amphiphilic polymer optionally combined with at least one anionic surfactant; the total content of anionic amphiphilic polymer(s) or anionic surfactant(s) is between 1% and 5% by weight relative to the inverse emulsion.

12. The process as claimed in claim 1, wherein the amount of outer surfactant and/or of outer amphiphilic polymer in the aqueous dilution phase is such that the amount of outer surfactant and/or of outer amphiphilic polymer is between 1% and 10% by weight relative to the outer aqueous phase of the dilute multiple emulsion.

13. The process as claimed in claim 1, wherein the amount of dilution water in step e) is such that the dilute multiple emulsion presents an inverse emulsion/outer aqueous phase weight ratio of between 10/90 and 50/50.

14. The process as claimed in claim 1, wherein the aqueous dilution phase comprises a salt which is an alkali metal halide, an alkaline-earth metal halide, a alkali metal sulfate, or an alkaline-earth metal sulfate, or a sugar, or a polysaccharide, in an amount such that of the combination of outer aqueous phase and aqueous dilution phase presents an osmotic pressure equilibrated with that of the inner aqueous phase.

15. The process as claimed in claim 1, wherein the outer aqueous phase or the aqueous dilution phase further comprises at least one water-soluble or water-dispersible compound, as additive for drying the multiple emulsion, which is:

a polymer obtained by polymerization of at least one aliphatic, cyclic or aromatic, linear or branched, ethylenically unsaturated monocarboxylic or polycarboxylic acid or anhydride monomer (I) and of at least one linear or branched, monoethylenically or polyethylenically unsaturated hydrocarbon-based monomer (II), or of at least one ethylenically unsaturated polyalkoxylated carboxylic acid ester monomer (Ill); or a polymer derived from the polymerization of at least one monomer (I), polypeptides of natural or synthetic origin, or highly depolymerized polysaccharides; said polymers optionally comprising at least one saturated or unsaturated, aromatic or nonaromatic $C_4$-$C_{30}$ hydrocarbon-based hydrophobic graft, optionally interrupted with one or more hetero atoms; said water-soluble or water-dispersible compound being in a content in the outer aqueous phase such that the content of this compound in the dried multiple emulsion is between 30% and 70% by weight of the dried multiple emulsion.

16. The process as claimed in claim 1, wherein the aqueous dilution phase further comprises a thickener which is a polymer extracted from plants and optionally modified, a polysaccharide of animal, plant or bacterial origin, said thickener being being in a content of between 0.1% and 2% by weight relative to the aqueous phase in the dilute multiple emulsion.

17. The process as claimed in claim 1, wherein the aqueous dilution phase further comprises a dispersed outer organic phase comprising a hydrophobic active material.

18. The process as claimed in claim 17, wherein the dispersed outer organic phase represents 1% to 50% by weight of the outer aqueous phase of the dilute multiple emulsion.

19. The process as claimed in claim 1, wherein the aqueous dilution phase further comprises at least one dispersed solid.

20. The process as claimed in claim 19, wherein the dispersed solid represents 1% to 50% by weight of the outer aqueous phase of the dilute multiple emulsion.

* * * * *